United States Patent
Farmer et al.

(10) Patent No.: US 11,396,623 B2
(45) Date of Patent: *Jul. 26, 2022

(54) MATERIALS AND METHODS FOR RECOVERING OIL FROM OIL SANDS

(71) Applicant: Locus Oil IP Company, LLC, Solon, OH (US)

(72) Inventors: Sean Farmer, North Miami Beach, FL (US); Ken Alibek, Solon, OH (US); Karthik N. Karathur, Solon, OH (US)

(73) Assignee: LOCUS OIL IP COMPANY, LLC, Solon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/646,472

(22) PCT Filed: Sep. 24, 2018

(86) PCT No.: PCT/US2018/052427
§ 371 (c)(1),
(2) Date: Mar. 11, 2020

(87) PCT Pub. No.: WO2019/067356
PCT Pub. Date: Apr. 4, 2019

(65) Prior Publication Data
US 2020/0291289 A1  Sep. 17, 2020

Related U.S. Application Data

(60) Provisional application No. 62/611,114, filed on Dec. 28, 2017, provisional application No. 62/563,981, filed on Sep. 27, 2017.

(51) Int. Cl.
| | |
|---|---|
| E21B 43/16 | (2006.01) |
| C09K 8/582 | (2006.01) |
| C09K 8/584 | (2006.01) |
| C12N 1/16 | (2006.01) |
| C10G 1/00 | (2006.01) |
| C10G 32/00 | (2006.01) |

(52) U.S. Cl.
CPC ............ *C09K 8/582* (2013.01); *C09K 8/584* (2013.01); *C10G 1/00* (2013.01); *C12N 1/16* (2013.01); *E21B 43/16* (2013.01); *C10G 32/00* (2013.01)

(58) Field of Classification Search
None
See application file for complete search history.

(56) References Cited

U.S. PATENT DOCUMENTS

| | | |
|---|---|---|
| 3,191,676 A | 6/1965 | Froning |
| 3,871,956 A | 3/1975 | Azarowics |
| 4,033,412 A * | 7/1977 | Barrett .................... E21B 43/16 |
| | | 166/267 |
| 4,450,908 A | 5/1984 | Hitzman |
| 4,487,262 A | 12/1984 | Venkatesan et al. |
| 4,522,261 A | 6/1985 | McInerney et al. |
| 4,561,501 A | 12/1985 | Shaw et al. |
| 4,793,826 A | 12/1988 | Hayes et al. |
| 4,905,761 A | 3/1990 | Bryant |
| 5,021,088 A | 6/1991 | Portier |
| 5,800,593 A | 9/1998 | Kohr |
| 5,869,325 A | 2/1999 | Crabtree et al. |
| 6,033,901 A | 3/2000 | Powell, Jr. |
| 7,472,747 B1 | 1/2009 | Brigmon et al. |
| 7,677,673 B2 * | 3/2010 | Tranquilla .......... E21B 43/2401 |
| | | 299/2 |
| 7,681,638 B2 | 3/2010 | Soni et al. |
| 8,188,012 B2 | 5/2012 | Weerasooriya et al. |
| 8,316,933 B2 | 11/2012 | Kohr |
| 9,422,470 B2 | 8/2016 | Xu et al. |
| 9,550,937 B2 | 1/2017 | Campbell et al. |
| 9,683,164 B2 | 6/2017 | Gunawan et al. |
| 9,725,986 B2 | 8/2017 | Xu et al. |
| 10,023,787 B2 | 7/2018 | Benoit et al. |
| 10,190,038 B2 | 1/2019 | Armstrong et al. |
| 2002/0037245 A1 | 3/2002 | Galina |
| 2005/0045325 A1 * | 3/2005 | Yu ....................... E21B 43/2406 |
| | | 166/245 |
| 2007/0092930 A1 | 4/2007 | Lal et al. |
| 2007/0151726 A1 | 7/2007 | Crews et al. |
| 2008/0051301 A1 * | 2/2008 | Chen ....................... C09K 8/74 |
| | | 507/244 |
| 2008/0167445 A1 | 7/2008 | Podella et al. |
| 2008/0302531 A1 | 12/2008 | Berger et al. |
| 2009/0029879 A1 | 1/2009 | Soni et al. |
| 2010/0044031 A1 | 2/2010 | Fallon et al. |
| 2010/0163230 A1 | 7/2010 | Kotlar |
| 2011/0067856 A1 * | 3/2011 | Kohr ....................... E21B 43/16 |
| | | 166/246 |
| 2011/0139262 A1 | 6/2011 | Aburto Anell et al. |
| 2011/0290482 A1 | 12/2011 | Weerasooriya et al. |

(Continued)

FOREIGN PATENT DOCUMENTS

| | | |
|---|---|---|
| CN | 102399547 A | 4/2012 |
| CN | 102766579 A | 11/2012 |
| CN | 102925397 A | 2/2013 |
| CN | 103449696 A | 12/2013 |
| CN | 104109646 A | 10/2014 |

(Continued)

OTHER PUBLICATIONS

Amani, H., et al., "Comparative study of biosurfactant producing bacteria in MEOR applications." Journal of Petroleum Science and Engineering. 2010, 75: 209-214.

(Continued)

*Primary Examiner* — Andrew Sue-Ako
(74) *Attorney, Agent, or Firm* — Saliwanchik, Lloyd & Eisenschenk

(57) ABSTRACT

The present invention provides environmentally-friendly compositions and methods for recovering oil from oil sands. The present invention can also be used for reducing the viscosity and/or increasing the API gravity of oil. In specific embodiments, the invention utilizes compositions comprising biochemical-producing microorganisms and microbial growth by-products, such as biosurfactants, as well as cavitation, to enhance oil recovery.

5 Claims, No Drawings

(56) References Cited

U.S. PATENT DOCUMENTS

| | | | |
|---|---|---|---|
| 2012/0055685 | A1 | 3/2012 | Sanders et al. |
| 2012/0122740 | A1 | 5/2012 | Roldan Carrillo et al. |
| 2012/0214713 | A1 | 8/2012 | Mu et al. |
| 2012/0292022 | A1 | 11/2012 | Choban et al. |
| 2013/0062053 | A1 | 3/2013 | Kohr et al. |
| 2014/0273150 | A1 | 9/2014 | Angel |
| 2014/0274823 | A1* | 9/2014 | Westenberg ............ C09K 8/58 507/262 |
| 2014/0305649 | A1 | 10/2014 | Tang et al. |
| 2014/0332212 | A1 | 11/2014 | Ayers et al. |
| 2015/0037302 | A1 | 2/2015 | Bralkowski et al. |
| 2015/0045290 | A1 | 2/2015 | Coutte et al. |
| 2015/0053545 | A1 | 2/2015 | Gordon et al. |
| 2015/0068950 | A1 | 3/2015 | See et al. |
| 2015/0259642 | A1 | 9/2015 | Sangwai et al. |
| 2015/0275328 | A1 | 10/2015 | Walder et al. |
| 2015/0300139 | A1 | 10/2015 | Armstrong et al. |
| 2016/0145487 | A1 | 5/2016 | Alam et al. |
| 2016/0160111 | A1 | 6/2016 | Smith et al. |
| 2016/0244347 | A1 | 8/2016 | Angel |
| 2016/0251565 | A1 | 9/2016 | Yangisawa et al. |
| 2017/0037301 | A1 | 2/2017 | Alwattari |
| 2017/0044424 | A1 | 2/2017 | Dwarakanath et al. |
| 2017/0138135 | A1* | 5/2017 | Almutairi ................ B09C 1/06 |
| 2018/0201531 | A1 | 7/2018 | Cohen et al. |
| 2018/0282608 | A1 | 10/2018 | Gopal et al. |
| 2019/0292436 | A1 | 9/2019 | Mason et al. |

FOREIGN PATENT DOCUMENTS

| | | |
|---|---|---|
| CN | 104974952 A | 10/2015 |
| CN | 105154050 A | 12/2015 |
| CN | 103614131 B | 1/2016 |
| CN | 105753283 A | 7/2016 |
| KR | 101481459 B1 | 1/2015 |
| WO | 2010111226 A2 | 9/2010 |
| WO | 2013110132 A1 | 8/2013 |
| WO | 2014152350 A1 | 9/2014 |
| WO | 2015093934 A1 | 6/2015 |
| WO | 2015167864 A1 | 11/2015 |
| WO | 2016196680 A1 | 12/2016 |
| WO | 2017040903 A1 | 3/2017 |
| WO | 2017044953 A1 | 3/2017 |
| WO | 2018107162 A1 | 6/2018 |

OTHER PUBLICATIONS

Castaneda, L.C., et al., "Current situation of emerging technologies for upgrading of heavy oils." Catalysis Today, 2014, 220-222: 248-273.

De Almeida, D., et al., "Biosurfactants: Promising Molecules for Petroleum Biotechnology Advances." Frontiers in Microbiology, Oct. 2016, 7(1718): 1-14.

De Brito, D., Biosurfactants from renewable raw materials, Universidade do Minho Departamento de Engenharia Biologica, Nov. 2013, pp. 1-93.

De Oliveira, M., et al., "Review: Sophorolipids A Promising Biosurfactant and it's Applications." International Journal of Advanced Biotechnology and Research, 2015, 6(2): 161-174.

Elshafie, A. E., et al., "Sophorolipids Production by Candida bombicola ATCC 22214 and its Potential Application in Microbial Enhanced Oil Recovery." Frontiers in Microbiology, Nov. 2015, 6(1324): 1-11.

Ghojavand, H. et al., "Isolation of thermotolerant, halotolerant, facultative biosurfactant-producing bacteria." Appl. Microbiol. Biotechnol, Oct. 2008, 80(6): Abstract, doi: 10,1007/s00253-008-1570-7.

Gudina, E., et al., "Biosurfactant-producing and oil-degrading Bacillus subtilis strains enhance oil recovery in laboratory sand-pack columns." Journal of Hazardous Materials, 2013, 261: 106-113.

Nur, H.A., et al., "*Saccharomyces cerevisiae* from Baker's Yeast for Lower Oil Viscosity and Beneficial Metabolite to Improve Oil Recovery: An Overview." Applied Mechanics and Materials, 2014, 625: 522-525.

Santos, D.K.F., et al., "Biosurfactants: Multifunctional Biomolecules of the 21st Century." International Journal of Molecular Sciences, 2016, 17(401): 1-31.

Sen, R., "Biosurfactants: Advances in Experimental Medicine and Biology." Landes Bioscience and Springer Science +Business Media, LLC, 2010, 672: 1-331.

Sharma, A. et al., "A study on biosurfactant production in *Lactobacillus* and *Bacillus* sp." Int. J. Curr. Microbiol. App. Sci., 2014, 3(11): 723-733.

Silva, R., et al., "Applications of Biosurfactants in the Petroleum Industry and the Remediation of Oil Spills." International Journal of Molecular Sciences, 2014, 15: 12523-12542.

Takahashi, M., et al., "Production of Sophorolipid Glycolipid Biosurfactants from Sugarcane Molasses Using Starmerella bombicola NBRC 10243." Journal of Oleo Science, 2011, 60(5): 267-2733.

Das, N., et al., "Review Article Microbial Degradation of Petroleum Hydrocarbon Contaminants: An Overview." Biotechnology Research International, 2011, 2011: 941810, pp. 1-13.

El-Sheshtawy, H.S., et al., "Production of biosurfactants by Bacillus licheniformis and Candida albicans for application in microbial enhanced oil recovery." Egyptian Journal of Petroleum, 2016, 25: 293-298.

E Silva, F.C.P.R.; et al., "Yeasts and bacterial biosurfactants as demulsifiers for petroleum derivative in seawater emulsions." AMB Express, 2017, 7(202): 1-13.

Ines, M., et al., "Glycolipids biosurfactants; potential related biomedical and biotechnical applications." Carbohydrate Research, 2015, 416: 59-69.

Kaur, K., et al., "Biosurfactant production by yeasts isolated from hydrocarbon polluted environments." Environ Monit Assess, 2017, 189 (603: 1-13.

Kurizman, C.P., et al., "Production of sophorolipid biosurfactants by multiple species of the *Starmerella* (Candida) bombicolayeast clade." FEMS Microbiol Lett, 2010, 311: 140-146.

Liu, X., et al., "Recovery of crude oil from oily sludge in an oilfield by sophorolipid." Petroleum Science and Technology, 2019, 37(13): 1582-1588.

Ma, X., et al., "Surface and biological activity of sophorolipid molecules produced by *Wickerhamiella domercqiae* var. *sophorolipid* CGMCC 1576." Journal of Colloid and Interface Science, 2012, 376: 165-172.

Pacwa-Plociniczak, M. et al., "Review: Environmental Applications of Biosurfactants: Recent Advances." Int. J. Mol. Sci., 2011, 12: 633-654.

Umar, Z.D., et al., "Rapid biodegradation of polycyclic aromatic hydrocarbons (PAHs) using effective Cronobacter sakazakii MM045 (KT933253)." MethodsX, 2017, 4: 104-117.

Wadekar, S., et al., "Sophorolipid Production by Starmerella bombicola (ATCC 22214) from Virgin and Waste Frying Oils, and the Effects of Activated Earth Treatment of the Waste Oils." J Am Oil Chern Soc, 2012, 89: 1029-1039.

Youssef, N., et al., "In Situ Biosurfactant Production by Bacillus Strains Injected into a Limestone Petroleum Reservoir." Applied and Environmental Microbiology, Feb. 2007, 73(4): 1239-1247.

Zafra, G., et al., "Biodegradation of polycyclic aromatic hydrocarbons by *Trichoderma* species: a mini review." Environ Sci Pollut Res, 2015, 22: 19426-19433.

\* cited by examiner

MATERIALS AND METHODS FOR RECOVERING OIL FROM OIL SANDS

CROSS-REFERENCE TO RELATED APPLICATIONS

This application is a National Stage Application of International Application No. PCT/US2018/052427, filed Sep. 24, 2018; which claims the benefit of U.S. provisional application Ser. Nos. 62/563,981, filed Sep. 27, 2017, and No. 62/611,114, filed Dec. 28, 2017, all of which are incorporated herein by reference in their entirety.

BACKGROUND OF THE INVENTION

"Heavy" and "extra heavy" crude oils are highly viscous with a density close to or exceeding water. Heavy oils are crudes that have API gravity less than 20° or viscosity higher than 200 cp. Extra heavy oil refers to petroleum with API gravity less than 12° and viscosity higher than 10,000 cp ("Heavy Oil" 2016). The viscosity of heavy crude oil makes it difficult to extract the oil from the ground and expensive to transport oil to processing facilities. For example, a significant amount of energy is required to pump oil with higher viscosity through pipelines to refineries and processing facilities. Furthermore, viscosity affects the speed at which crude oil can be pumped from a well, with more viscous oils contributing to a decrease in overall productivity for an oil field.

Some oils have naturally higher viscosities than others. "Light" crude oil, or that which has low density and which flows freely at room temperature, has low viscosity and high API gravity due to its higher proportion of light hydrocarbon fractions. However, low viscosity crude oils can weather over time into more viscous forms.

One source of heavy oil is found in the regions containing oil sands, or tar sands. Oil sands are a combination of clay, sand, water and bitumen—a heavy, highly viscous type of oil. The largest oil sand deposits in the world can be found in Alberta, Canada and in Venezuela. Other deposits are located in the Middle east and the United States, concentrated primarily in eastern Utah. The bitumen in oil sands cannot be pumped from the ground in its natural state by conventional oil recovery means; however, much of the world's oil (more than 2 trillion barrels) is in the form of oil sands. Some of this oil requires complex extraction techniques, or is not recoverable at all.

Currently, oil is not produced from oil sands on a significant commercial level in the United States, and in fact, only Canada has a large-scale commercial tar sands industry, though a small amount of oil from oil sands is produced commercially in Venezuela. Due to the high demand for crude oil, however, and the desire to keep costs of oil low, oil sands-based oil production is becoming an increasingly attractive, and even necessary, alternative to conventional oil recovery.

The oil that is recovered from oil sands can be processed into products that are similar to oil pumped from conventional oil wells, but extracting oil from oil sands is far more complex than conventional oil recovery. Extraction and separation systems are required to separate the bitumen from clay, sand and water that make up the oil sands. Bitumen also requires additional upgrading before it can be refined because of its high viscosity, and additional treatment to make it transportable by pipelines. About two tons of tar sands are required to produce one barrel of oil.

Oil sands are currently extracted both by mining and in situ recovery methods. Open pit mining techniques can be used to extract oil sand deposits near the earth's surface, typically within 200 feet of the earth's surface. About 20% of oil sands lie within this range, with roughly 75% of the bitumen recoverable from the sand. For the 80% of oil sands reserves that are too deep to be mined, in situ production methods are used.

Due to the depth of the reserves, recovery rates for the methods of extracting bitumen vary. Mining allows operators to recover more of the oil, while using less energy. Drilling is a more energy-intensive process but allows for a smaller footprint. Drilling methods cannot be used in mining areas, and vice-versa.

Open mining systems use large hydraulic and electrically-powered shovels to dig up oil sands and load them into massive trucks. After mining, the oil sands are transported to an extraction plant, where a hot water process separates the bitumen from the sand, water and minerals. The separation takes place in separation cells. Hot water is added to the sand, and the resulting slurry is piped to the extraction plant where it is agitated. The combination of hot water and agitation releases bitumen from the oil sand and causes tiny air bubbles to attach to the bitumen droplets, which float to the top of the separation vessel and can be skimmed off. Further processing removes residual water and solids. The bitumen is then transported and eventually upgraded into synthetic crude oil. After oil extraction, the spent sand and other materials are returned to the mine, which is eventually reclaimed.

In in situ systems, advanced technology is used to inject steam, combustion or other sources of heat into the reservoir. The heat warms the bitumen so it can be pumped to the surface through recovery wells. Advances in technology, such as directional drilling, enable in situ operations to drill multiple wells (sometimes more than 20) from a single location, further reducing surface disturbance.

The majority of in situ operations use steam-assisted gravity drainage, or SAGD. This method involves pumping steam underground through a horizontal well to liquefy the bitumen, which is then pumped to the surface through a second recovery well. A second method, cyclic steam stimulation (CSS), pumps steam down a vertical well to soak or liquefy the bitumen, which is then pumped to the surface through the same well. This technique is repeated until the oil is removed.

Both mining and processing of oil sands involve a variety of environmental impacts, such as climate change and greenhouse gas emissions; disturbance of mined land; impacts on wildlife; and impacts on air and water quality. The development of a commercial oil sands industry in certain areas, for example, the United States, would also have significant social and economic impacts on local communities. Of special concern in the relatively arid western United States is the large amount of water required for oil sands processing; currently, oil sands extraction and processing require several barrels of water for each barrel of oil produced, though some of the water can be recycled.

Furthermore, heavy oil and bitumen must be processed after they have been recovered from oil sands. Many refineries were designed to process only conventional light crude oils, some heavy oils and a small fraction of the bitumen produced, to upgraded to create synthetic crude oil. Upgrading can occur at or near the producing area or the refinery.

Upgrading uses temperature, pressure and catalysts to crack the large molecules into smaller ones. Adding hydrogen or removing carbon from the oil creates hydrocarbon molecules like those in light oil. Upgraded oil is used as a replacement for conventional crude oil to make gasoline, diesel, jet fuel and heating oil.

Heavy and extra heavy crude oils are a major potential energy resource. Forty percent of the world's total oil reserves are heavy and extra heavy oil, accounting for 3.6-5.2 trillion bbl of oil. Thus, recovery of these highly viscous hydrocarbons could have major economic significance. However, most heavy and extra heavy oils are not recoverable by conventional methods. Furthermore, because heavy crude oils cannot easily flow through pipelines, transporting the oil often requires employing burdensome methods, such as carrying the oil using tanker trucks.

Efficient production of oil and other hydrocarbons is crucial to meet the high demand for such products. Because of the difficulties and costs of extracting oil from oil sands, and further because of the difficulties of pumping and transporting heavy oil, improved methods of oil recovery and processing are needed in order to enable the utilization of the world's heavy and viscous oil reserves.

BRIEF SUMMARY OF THE INVENTION

The subject invention provides environmentally-friendly, cost-efficient materials and methods for enhancing oil recovery and improving the transportation of oil. In specific embodiments, the subject invention provides microbe-based compositions and methods for recovering oil from oil sands and for reducing the viscosity and/or increasing the API gravity of heavy crude oil.

In certain embodiments, the subject invention provides materials and methods for improving oil production by treating oil sands and/or an oil sand-containing site (e.g., a formation) with a microbe-based composition capable of separating oil from the oil sands. Advantageously, the subject invention can be used without increasing the total acid number (TAN) of crude oil.

In certain embodiments, the subject invention can also improve oil production and transportation by reducing the viscosity of oil and/or increasing the API gravity of oil.

In preferred embodiments, the subject invention provides microbe-based compositions, comprising one or more microorganisms and/or one or more microbial growth by-products. The composition may also comprise the fermentation medium in which the microorganisms and/or growth by-products were produced. In one embodiment, the composition comprises a microbial growth by-product without the microorganism.

The microbial growth by-products can be those produced by the microorganisms of the composition, and/or they can be produced elsewhere and added to the composition.

In one embodiment, the microbial growth by-product is a biosurfactant. The biosurfactants can be purified or a crude form, where the crude form comprises, for example, a mixture comprising biosurfactant in fermentation medium resulting from cultivation of a biosurfactant-producing microbe. This crude form biosurfactant solution can comprise from about 0.001% to about 99%, from about 25% to about 85%, from about 30% to about 70%, from about 35% to about 65%, from about 40% to about 60%, from about 45% to about 55%, or about 50% biosurfactant.

The biosurfactants can be selected from glycolipids, e.g., sophorolipids, mannosylerythritol lipids, trehalose lipids and rhamnolipids, and lipopeptides, e.g., surfactin, iturin, lichenysin and fengycin.

In one exemplary embodiment, the composition can comprise sophorolipids (SLPs) and/or mannosylerythritol lipids (MELs) at a concentration of, for example, 0.1% to 5.0%, even up to 10% or higher.

In one embodiment, the composition comprises one or more bases such as, for example, potassium hydroxide, sodium hydroxide and/or ammonium hydroxide. Preferably, the amount of base in the composition is enough to bring the pH of the composition into a basic range, from about 7.0 to about 10.5, more preferably from about 10.0 to about 10.5.

In certain embodiments, the microorganism according to the subject invention is a biochemical-producing microorganism. In specific embodiments, the microbe is a biosurfactant-producing yeast, such as, for example, *Starmerella bombicola*. In another embodiment, the microorganism is *Wickerhamomyces anomalus* (*Pichia anomala*), *Pichia guilliermondii, Pichia occidentalis*, or any yeast species closely related thereto. The microorganisms may be live (or viable) or inactive in the composition.

In certain embodiments, the microbe-based composition is capable of increasing the wettability of the oil sands, allowing for detachment of the oil and/or bitumen from clay, sand, and other minerals present in oil sands. In certain other embodiments, the microbe-based composition, as well as the use of cavitation, can also reduce the viscosity and/or increase the API gravity of the oil; thus, use of a composition according to the subject invention can improve the ability to recover and/or transport heavy oil.

In certain embodiments, the microbe-based compositions according to the subject invention can be superior to, for example, purified microbial metabolites alone, due to, for example, the advantageous properties of yeast cell walls. These properties include high concentrations of mannoprotein as a part of yeast cell wall's outer surface (mannoprotein is a highly effective bioemulsifier) and the presence of the biopolymer beta-glucan (also an effective emulsifier) in yeast cell walls. Additionally, the yeast fermentation product further can comprise a variety of metabolites in the culture, including biosurfactants, which are capable of reducing both surface and interfacial tension, emulsifying oil, and improving oil mobility, as well as others (e.g., lactic acid, ethyl acetate, ethanol, oxidizing enzymes, hydrolyzing enzymes, etc.).

In one embodiment the subject invention provides improved methods of enhanced oil recovery. In certain embodiments, the subject invention provides improved methods of recovering oil from oil sands or a formation containing oil sands, wherein the method comprises: applying a microbe-based composition comprising one or more biochemical-producing microorganisms and/or their growth by-products to the oil sands, or to the formation containing oil sands, thereby causing the oil to detach from the oil sands; and recovering the detached oil from the oil sands or from the formation. In certain embodiments, the recovered oil is bitumen or heavy oil.

In certain embodiments, the method utilizes a microbe-based composition comprising *Starmerella bombicola* culture to detach the oil from the oil sands. In one embodiment the microbe-based composition comprises the fermentation medium in which the microorganism and/or microbial growth by-product was produced. In one embodiment, the microbe-based composition comprises a microbial growth by-product without the microorganism that produced it.

In one embodiment, the method can comprise applying biosurfactants to the oil sands and/or oil sands formation. For example, pure or crude form biosurfactants can be applied to not only enhance detachment of oil from oil sands, but also to enhance the recovery of oil by reducing the interfacial tension between the oil and oil sands and/or between oil and formation rock.

In one embodiment, the method can further comprise applying a basic substance to the oil sands or oil sands formation with the microbe-based composition and/or biosurfactants. The basic substance preferably keeps the composition at a pH of about 7.0 to 10.5, more preferably about 10.0 to 10.5. The basic substance can be, for example, potassium hydroxide, sodium hydroxide and/or ammonium hydroxide.

In certain embodiments, the method further comprises subjecting the oil sands to cavitation after applying the microbe-based composition thereto. In one embodiment, the oil sands have been mined from the earth prior to being treated according to the subject invention.

In one embodiment, the method can further comprise treating the oil recovered from the oil sands and/or oil sands formation to reduce the viscosity and/or increase the API gravity of the oil. For example, a microbe-based composition of the subject invention can be applied directly to the recovered oil, followed by, optionally, subjecting the oil to cavitation. Preferably, the microbe-based composition utilized for reducing viscosity and/or increasing API gravity of oil comprises a *Pichia* yeast culture, such as *Pichia anomala* (*Wickerhamomyces anomalus*), *Pichia guilliermondii*, and/or *Pichia occidentalis*.

Cavitation can be carried out using machinery known in the art, and can comprise, for example, hydrodynamic or ultrasonic methods. Furthermore, cavitation can be applied to heavy crude oil at any point during the oil recovery and transport chain of operation, for example, after recovery from a well and before being placed in a collection storage tank; during storage; after storage and before being transported in a tanker; during transportation; and before the refining process.

In one embodiment, the present invention allows for improved transportation of oil. By reducing the viscosity and/or increasing the API gravity of heavy oil, oils can be more efficiently transported by pipeline, tanker trucks and/or cargo trains.

Advantageously, the present invention can be used without releasing large quantities of inorganic compounds into the environment. Additionally, the compositions and methods utilize components that are biodegradable and toxicologically safe. Thus, the present invention can be used in all possible operations of oil and gas production as a "green" treatment.

DETAILED DESCRIPTION

The subject invention provides environmentally-friendly, cost-efficient materials and methods for enhancing oil recovery and improving the transportation of oil. In specific embodiments, the subject invention provides microbe-based compositions and methods for recovering oil from oil sands and for reducing the viscosity and/or increasing the API gravity of heavy crude oil.

In preferred embodiments, the subject invention provides microbe-based compositions, comprising one or more microorganisms and/or one or more microbial growth by-products. The composition may also comprise the fermentation medium in which the microorganisms and/or growth by-products were produced. In one embodiment, the composition comprises a microbial growth by-product without the microorganism.

The microbial growth by-products can be those produced by the microorganisms of the composition, and/or they can be produced elsewhere and added to the composition.

In one embodiment, the microbial growth by-product is a biosurfactant. The biosurfactants can be selected from glycolipids, e.g., sophorolipids, mannosylerythritol lipids, trehalose lipids and rhamnolipids, and lipopeptides, e.g., surfactin, iturin, lichenysin and fengycin.

In one exemplary embodiment, the composition can comprise sophorolipids (SLPs) and/or mannosylerythritol lipids (MELs) at a concentration of, for example, 0.1% to 5.0%, even up to 10.0% or higher.

In one embodiment, the composition comprises one or more bases such as, for example, potassium hydroxide, sodium hydroxide and/or ammonium hydroxide. Preferably, the amount of base in the composition is enough to bring the pH of the composition into a basic range, from about 7.0 to about 10.5, more preferably from about 10.0 to about 10.5.

In certain embodiments, the microorganism according to the subject invention is a biochemical-producing microorganism. In specific embodiments, the microbe is a biosurfactant-producing yeast, such as, for example, *Starmerella bombicola*. In another embodiment, the microorganism is *Wickerhamomyces anomalus*(*Pichia anomala*), *Pichia guilliermondii*, *Pichia occidentalis*, or any yeast species closely related thereto. The microorganisms may be live (or viable) or inactive in the composition.

In one embodiment the subject invention provides improved methods of recovering oil from oil sands or a formation containing oil sands, wherein the method comprises: applying a microbe-based composition comprising one or more biochemical-producing microorganisms and/or their growth by-products to the oil sands, or to the formation containing oil sands, thereby causing the oil to detach from the oil sands; and recovering the detached oil from the oil sands or from the formation. In certain embodiments, the recovered oil is bitumen or heavy oil.

In certain embodiments, the method utilizes a microbe-based composition comprising *Starmerella bombicola* culture to detach the oil from the oil sands. In one embodiment the microbe-based composition comprises the fermentation medium in which the microorganism and/or microbial growth by-product was produced. In one embodiment, the microbe-based composition comprises a microbial growth by-product without the microorganism that produced it.

In one embodiment, the method can comprise applying biosurfactants to the oil sands and/or oil sands formation. In another embodiment, the method can further comprise applying a basic substance to the oil sands or oil sands formation.

In certain embodiments, the method further comprises subjecting the oil sands to cavitation after applying the microbe-based composition thereto. In one embodiment, the oil sands have been mined from the earth prior to being treated according to the subject invention.

In one embodiment, the method can further comprise treating the oil recovered from the oil sands and/or oil sands formation to reduce the viscosity and/or increase the API gravity of the oil. For example, a microbe-based composition of the subject invention can be applied directly to the recovered oil, followed by, optionally, subjecting the oil to cavitation. Preferably, the microbe-based composition utilized for reducing viscosity and/or increasing API gravity of oil comprises a *Pichia* yeast culture, such as *Pichia anomala* (*Wickerhamomyces anomalus*), *Pichia guilliermondii*, and/or *Pichia occidentalis*.

In one embodiment, the present invention allows for improved transportation of oil. By reducing the viscosity and/or increasing the API gravity of heavy oil, oils can be more efficiently transported by pipeline, tanker trucks and/or cargo trains.

Selected Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. The microbes may be absent from (i.e. separated from) the composition, or they may be present, with broth in which they were grown, in the microbe-based composition. The cells may be present at, for example, a concentration of $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{13}$ or $1 \times 10^{13}$ or more cells per milliliter of the composition.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, added nutrients to support further microbial growth, non-nutrient growth enhancers, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, "harvested" refers to removing some or all of the microbe-based composition from a growth vessel.

As used herein, a "biofilm" is a complex aggregate of microorganisms, such as bacteria, wherein the cells adhere to each other. The cells in biofilms are physiologically distinct from planktonic cells of the same organism, which are single cells that can float or swim in liquid medium.

As used herein, an "isolated" or "purified" nucleic acid molecule, polynucleotide, polypeptide, protein, organic compound such as a small molecule (e.g., those described below), or other compound is substantially free of other compounds, such as cellular material, with which it is associated in nature. For example, a purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. A purified or isolated microbial strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (e.g., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites can include, but are not limited to, enzymes, toxins, acids, solvents, alcohols, proteins, carbohydrates, vitamins, minerals, microelements, amino acids, polymers, and surfactants.

By "modulate" is meant alter (e.g., increase or decrease). Such alterations are detected by standard art known methods such as those described herein.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 1%, 5%, 10%, 25%, 50%, 75%, or 100%.

By "reference" is meant a standard or control condition.

By "salt-tolerant" is meant a microbial strain capable of growing in a sodium chloride concentration of fifteen (15) percent or greater. In a specific embodiment, "salt-tolerant" refers to the ability to grow in 150 g/L or more of NaCl.

By "surfactant" is meant a compound that lowers the surface tension (or interfacial tension) between two liquids or between a liquid and a solid. Surfactants act as, for example, detergents, wetting agents, emulsifiers, foaming agents, and dispersants.

A "biosurfactant" is a surface-active substance produced by a living cell. Biosurfactants are biodegradable and can be produced efficiently using selected organisms on renewable substrates. All biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances, increase the water bioavailability of such substances, and can even change the properties of bacterial cell surfaces.

Biosurfactants include low molecular weight glycolipids (e.g., rhamnolipids, sophorolipids, trehalose lipids and mannosylerythritol lipids), lipopeptides (e.g., surfactin, iturin, fengycin and lichenysin), flavolipids, phospholipids, and high molecular weight polymers such as lipoproteins, lipopolysaccharide-protein complexes, and polysaccharide-protein-fatty acid complexes. The common lipophilic moiety of a biosurfactant molecule is the hydrocarbon chain of a fatty acid, whereas the hydrophilic part is formed by ester or alcohol groups of neutral lipids, by the carboxylate group of fatty acids or amino acids (or peptides), organic acid in the case of flavolipids, or, in the case of glycolipids, by the carbohydrate.

As used herein, "heavy oil" or "heavy hydrocarbons" mean viscous hydrocarbon substances. Heavy hydrocarbons may comprise highly viscous hydrocarbons such as heavy oil, extra heavy oil, bitumen, tar, petcoke, asphaltenes and/or asphalt. Heavy oils and extra heavy oils are highly viscous with a density close to or even exceeding water. The phrase "heavy oil" as used herein also includes "extra heavy oil." Heavy hydrocarbons may comprise moderate to high quantities of paraffins, resins and asphaltenes, as well as smaller concentrations of sulfur, oxygen, and nitrogen. Heavy hydrocarbons may also include aromatics or other complex ring hydrocarbons. Additional elements, e.g., metals, may also be present in heavy hydrocarbons in trace amounts.

Heavy hydrocarbons may be classified by API gravity. API gravity is a measure of how heavy or light a petroleum liquid is compared to water, and is used to compare densities of the petroleum liquids. An API greater than 10° means the fluid is lighter than water and an API less than 10° means the fluid will sink in water. Heavy hydrocarbons generally have an API gravity below about 20° or lower. Heavy oil, for example, generally has an API gravity of about 12-20°, whereas extra heavy oil generally has an API gravity below about 12°. The viscosity of heavy hydrocarbons, on the other hand, is generally greater than about 200 cp at reservoir conditions, and that of extra heavy oil is generally about 10,000 cp or more. (For reference, as used herein, "light oil" or "light hydrocarbons" have an API gravity above 20°, preferably above about 25°, even more preferably above 30° to 31°, and a viscosity of about 1 to 100 cp).

As used herein, "upgrading" or "converting" or "improving the quality of" or "increasing the value of" heavy oil and/or hydrocarbons means changing the structure of the hydrocarbons and/or the contents of the oil in such a way as to increase its overall utility to consumers, and thus, its value to producers. For example, the BTU, i.e., energy or heat content, of the oil can be increased, thus increasing the value of heavy crude before it is sold to refineries. This can also benefit oil refineries who can buy less expensive heavy crude and convert it to a more usable product, such as, for example, road asphalt, using the subject methods and compositions. Upgrading can also involve increasing the API gravity, reducing viscosity, and/or reducing the impurities content of heavy hydrocarbons. An impurity is often a free radical that attaches to large hydrocarbon molecules. Typical impurities found in heavy oil can include, for example, sulfur or hydrogen sulfide, ash, nitrogen, heavy metals (e.g., vanadium, nickel), olefins, aromatics, naphthenes, and asphaltenes.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "an" and "the" understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 01%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

Microbe-Based Compositions

The present invention provides compositions for enhancing oil recovery. In certain embodiments, compositions are provided for detaching oil from oil sands and recovery heavy oils from oil sands-containing sites. In some embodiments, compositions are provided for decreasing the viscosity and/or increasing the API gravity of heavy oils and/or bitumens. Furthermore, the compositions can be used to improve the efficiency of oil transportation.

In preferred embodiments, the subject invention provides microbe-based compositions comprising one or more microorganisms and/or one or more microbial growth by-products. The composition may also comprise the fermentation medium in which the microorganisms and/or growth by-products were produced. In one embodiment, the composition comprises a microbial growth by-product without the microorganism.

In one embodiment, the microorganism of the subject compositions is a biochemical-producing yeast or bacterium. In certain embodiments, the microorganism is *Starmerella bombicola*, which is a yeast capable of producing a culture containing sophorolipids.

In certain embodiments, the microorganism is a *Pichia* yeast, such as, for example, *Wickerhamomyces anomalus* (*Pichia anomala*), *Pichia guilliermondii* and/or *Pichia occidentalis*, or any yeast species closely related thereto. These yeasts are capable of producing, for example, oxidizing and/or hydrolyzing enzymes capable, which can be useful for converting heavy oils into lighter oils.

In one embodiment, the microorganism is a bacteria, such as a strain of *Bacillus*. In a specific embodiment, the strain is a strain of *B. subtilis*, such as, example, *B. subtilis* var. *locuses* strains B1 and B2, which are effective producers of surfactin. In some embodiments, the strains of *Bacillus* are "surfactant over-producing," meaning the strain may produce at least 0.1-10 g/L, e.g., 0.5-1 g/L surfactant by-products, or least 10%, 25%, 50%, 100%, 2-fold, 5-fold, 7.5 fold, 10-fold, 12-fold, 15-fold or more compared to other oil-recovery microbial strains.

The microbe-based composition can comprise fermentation medium containing live or inactive microbes and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

Advantageously, in accordance with the subject invention, the microbe-based composition may comprise the medium in which the microbes were grown.

The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween. The biomass content of the fermentation broth may be, for example from 5 g/l to 180 g/l or more. In one embodiment, the solids content of the broth is from 10 g/l to 150 g/l.

In the case of a dried product, or a culture produced using solid state fermentation, the cell concentration may be, for example, $1 \times 10^9$, $1 \times 10^{10}$, $1 \times 10^{11}$, $1 \times 10^{12}$ or $1 \times 10^{13}$ cells per gram of final dried product.

The microorganisms in the microbe-based product may be in an active or inactive form, in spore form, mycelial form, or any other form of microbial propagule. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

The microbes and/or medium can be removed from the growth vessel in which cultivation occurs and transferred via, for example, piping for immediate use.

The microbial growth by-product produced by microorganisms of interest may be retained in the microorganisms or secreted into the growth medium. The microbial growth by-products can also be produced elsewhere and added to the composition.

In one embodiment, the microbial growth by-product is a biosurfactant. The biosurfactants can be purified or a crude form, where the crude form comprises, for example, a mixture comprising biosurfactant in fermentation medium resulting from cultivation of a biosurfactant-producing microbe. This crude form biosurfactant solution can comprise from about 0.001% to about 99%, from about 25% to about 85%, from about 30% to about 70%, from about 35% to about 65%, from about 40% to about 60%, from about 45% to about 55%, or about 50% biosurfactant.

Microbial biosurfactants are produced by a variety of microorganisms such as bacteria, fungi, and yeasts. Exemplary biosurfactant-producing microorganisms include *Pseudomonas* species (*P. aeruginosa, P. putida, P. florescens, P. fragi, P. syringae*); *Flavobacterium* spp.; *Bacillus* spp. (*B. subtilis, B. pumillus, B. cereus, B. licheniformis*); *Wickerhamomyces* spp., *Pichia* spp., *Candida* spp. (*C. albicans, C. apicola, C. rugosa, C. tropicalis, C. lipolytica, C. torulopsis*); *Rhodococcus* spp.; *Arthrobacter* spp.; *Campylobacter* spp.; *Cornybacterium* spp. and so on. The biosurfactants may be obtained by fermentation processes known in the art.

Safe, effective microbial biosurfactants reduce the surface and interfacial tensions between the molecules of liquids, solids, and gases. They are biodegradable and can be produced efficiently using selected organisms on renewable substrates. Most biosurfactant-producing organisms produce biosurfactants in response to the presence of a hydrocarbon source (e.g. oils, sugar, glycerol, etc.) in the growing media.

Biosurfactants according to the subject invention include, for example, low-molecular-weight glycolipids (GLs), lipopeptides (LPs), flavolipids (FLs), phospholipids, and high-molecular-weight polymers such as lipoproteins, lipopolysaccharide-protein complexes, and polysaccharide-protein-fatty acid complexes.

In one embodiment, the microbial biosurfactant is a glycolipid such as a rhamnolipid (RLP), sophorolipid (SLP), trehalose lipid (TL) or mannosylerythritol lipids (MEL). In one embodiment, the microbial biosurfactant is a lipopeptide, such as surfactin, iturin, lichenysin or fengycin.

In one embodiment, biosurfactants are added either individually or as a mixture, for example, a mixture comprising SLP and/or MEL. The biosurfactants may be mixed at any ratio as long as the composition contains the active components, i.e., the one or more biosurfactants, at concentration of 0.01 to 90% by weight (wt %), preferably 0.1 to 50 wt %, and more preferably 0.1 to 20 wt %. In another embodiment, purified biosurfactants may be in combination with an accepted carrier, in that biosurfactants may be presented at concentrations of 0.0001 to 50% (v/v), preferably, 0.005 to 20% (v/v), more preferably, 0.001 to 5% (v/v).

In one exemplary embodiment, the composition can comprise sophorolipids (SLPs) and/or mannosylerythritol lipids (MELs) at a concentration of, for example, 0.1% to 5.0%, even up to 10.0% or higher.

In a further embodiment, the composition can comprise a pH adjusting agent, such as, for example, sodium hydroxide, potassium hydroxide, ammonium hydroxide, potassium carbonate or bicarbonate, hydrochloric acid, nitric acid, sulfuric acid or mixtures thereof. In a preferred embodiment, the pH adjuster is a base, such as sodium hydroxide, potassium hydroxide and/or ammonium hydroxide.

In a preferred embodiment, the pH adjuster is added such that the pH of the microbe-based composition ranges from about 7.0 to 10.5, more preferably from about 10.0 to 10.5.

In certain embodiments, the microbe-based compositions according to the subject invention can be superior to, for example, purified microbial metabolites alone, due to, for example, the advantageous properties of yeast cell walls. These properties include high concentrations of mannoprotein as a part of yeast cell wall's outer surface (mannoprotein is a highly effective bioemulsifier) and the presence of the biopolymer beta-glucan (also an effective emulsifier) in yeast cell walls. Additionally, the yeast fermentation products further can comprise a variety of metabolites in the culture, including biosurfactants, which are capable of reducing both surface and interfacial tension, emulsifying oil, and improving oil mobility, as well as others (e.g., lactic acid, ethyl acetate, ethanol, oxidizing enzymes, hydrolyzing enzymes, etc.).

Microbial Strains Grown in Accordance with the Subject Invention

The microorganisms according to the methods of the subject invention can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microorganism is any yeast or fungus. Examples of yeast and fungus species suitable for use according to the current invention, include, but are not limited to, *Acaulospora, Aspergillus, Aureobasidium*(e.g., *A. pullulans*), *Blakeslea, Candida*(e.g., *C. albicans, C. api-* cola), *Debaryomyces*(e.g., *D. hansenii*), *Entomophthora*, *Fusarium*, *Hanseniaspora*(e.g., *H. uvarum*), *Hansenula*, *Issatchenkia*, *Kluyveromyces*, *Mortierella*, *Mucor*(e.g., *M piriformis*), *Penicillium*, *Phythium*, *Phycomyces*, *Pichia* (e.g., *P. anomala*, *P. guielliermondii*, *P. occidentalis*, *P. kudriavzevii*), *Pseudozyma*(e.g., *P. aphidis*), *Rhizopus*, *Saccharomyces*(*S. cerevisiae*, *S. boulardii sequela*, *S. torula*), *Starmerella*(e.g., *S. bombicola*), *Torulopsis*, *Thraustochytrium*, *Trichoderma*(e.g., *T. reesei*, *T. harzianum*, *T virens*), *Ustilago*(e.g., *U maydis*), *Wickerhamomyces*(e.g., *W anomalus*), *Williopsis*, *Zygosaccharomyces*(e.g., *Z. bailii*).

In certain embodiments, the microorganism is any yeast known as a "killer yeast" characterized by its secretion of toxic proteins or glycoproteins, to which the strain itself is immune. The exotoxins secreted by killer yeasts are capable of killing other strains of yeast, fungi, or bacteria. Killer yeasts can include, for example, *Candida*(e.g., *C. nodaensis*), *Cryptococcus*, *Debaryomyces*(e.g., *D. hansenii*), *Hanseniaspora*, (e.g., *H uvarum*), *Hansenula*, *Kluyveromyces* (e.g., *K. phaffii*), *Pichia*(e.g., *P. anomala*, *P. guielliermondii*, *P. occidentalis*, *P. kudriavzevii*), *Saccharomyces*(e.g., *S. cerevisiae*), *Torulopsis*, *Ustilago*(e.g., *U. maydis*), *Wickerhamomyces*(e.g., *W anomalus*), *Williopsis*(e.g., *W mrakii*), *Zygosaccharomyces*(e.g., *Z. bailii*), and others.

In one embodiment, the microorganism is *Starmerella bombicola*. In one embodiment, the microorganism is a *Pichia* yeast, such as, for example, *Wickerhamomyces anomalus*(*Pichia anomala*), *Pichia guilliermondii*, *Pichia occidentalis* and/or or any yeast species closely related thereto.

In certain embodiments, the microorganisms are bacteria, including Gram-positive and Gram-negative bacteria. The bacteria may be, for example *Acinetobacter*(e.g., *A. calcoaceticus*, *A. baumannii*, *A. venetianus*), *Agrobacterium* (e.g., *A. radiobacter*), *Azobacter*(e.g., *A. vinelandii*, *A. chroococcum*), *Azospirillum*(e.g., *A. brasiliensis*), *Bacillus* (e.g., *B. subtilis*, *B. licheniformis*, *B. firmus*, *B. laterosporus*, *B. megaterium*, *B. amyloliquefaciens*), *Clostridium* spp. (*C. butyricum*, *C. tyrobutyricum*, *C. acetobutyricum*, and *C. beijerinckii*), *Pseudomonas*(e.g., *P. chlororaphis* subsp. aureofaciens (*Kluyver*)), *Ralslonia*(e.g., *R eulropha*), *Rhizobium*, *Rhodospirillum* (e.g., *R. rubrum*), and/or *Sphingomonas paucimobilis*.

In one embodiment, the bacteria is a strain of *Bacillus*. Preferably, the strain is a strain of *B. subtilis*, such as, for example, *B. subtilis* var. *locuses* B1 or B2, which are effective producers of, for example, surfactin and other lipopeptides, as well as biopolymers. In this regard, WO 2017/044953 is incorporated herein, in its entirety, by reference.

In certain embodiments, the present invention utilizes *Bacillus subtilis* strains with enhanced biosurfactant production compared to wild type *Bacillus subtilis* as well as compared to other microbes used in oil recovery. In certain embodiments, the *Bacillus subtilis* strains are salt tolerant. In a specific embodiment, salt tolerant refers to the ability to grow in 150 g/L, or 15%, or more of NaCl.

In certain embodiments, the *Bacillus subtilis* strains are capable of thriving under low oxygen conditions. The strains are also capable of growing under anaerobic conditions.

In certain embodiments, the *Bacillus subtilis* strains have increased biopolymer, solvent and/or enzyme production. The *Bacillus subtilis*B series strains can also be used for producing enzymes that degrade or metabolize oil or other petroleum products.

Production of Microorganisms

The subject invention utilizes methods for cultivation of microorganisms and production of microbial metabolites and/or other by-products of microbial growth. The subject invention further utilizes cultivation processes that are suitable for cultivation of microorganisms and production of microbial metabolites on a desired scale. These cultivation processes include, but are not limited to, submerged cultivation/fermentation, solid state fermentation (SSF), and combinations, hybrids, and/or modifications thereof.

The subject invention provides methods for cultivation of microorganisms and production of microbial metabolites and/or other by-products of microbial growth. In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

In certain embodiments, a microbe growth facility produces fresh, high-density microorganisms and/or microbial growth by-products of interest on a desired scale. The microbe growth facility may be located at or near the site of application, or at a different location. The facility produces high-density microbe-based compositions in batch, quasi-continuous, or continuous cultivation.

In certain embodiments, the microbe growth facilities of the subject invention can be located at or near the location where the microbe-based product will be used (e.g., at or near an oil well) For example, the microbe growth facility may be less than 300, 250, 200, 150, 100, 75, 50, 25, 15, 10, 5, 3, or 1 mile from the location of use.

The microbe growth facilities can produce fresh, microbe-based compositions, comprising the microbes themselves, microbial metabolites, and/or other components of the broth in which the microbes are grown. If desired, the compositions can have a high density of vegetative cells or a mixture of vegetative cells, spores, conidia, mycelia and/or other microbial propagules. Advantageously, the compositions can be tailored for use at a specified location. In one embodiment, the microbe growth facility is located on, or near, a site where the microbe-based products will be used.

Advantageously, in preferred embodiments, the methods of the subject invention harness the power of naturally-occurring local microorganisms and their metabolic by-products to improve oil production, transmission and/or refining. Local microbes can be identified based on, for example, salt tolerance, ability to grow at high temperatures, and the use of genetic identification of the sequences described herein.

The microbe growth facilities provide manufacturing versatility by their ability to tailor the microbe-based products to improve synergies with destination geographies. The microbe growth facilities may operate off the grid by utilizing, for example, solar, wind and/or hydroelectric power. Thus, the microbe-based compositions can be produced in remote locations.

Regardless of the location of fermentation, the growth vessel used for growing microorganisms can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

The method can provide oxygenation to the growing culture. One embodiment utilizes slow motion of air to remove low-oxygen containing air and introduce oxygenated air. In the case of submerged fermentation or modifications thereof, the oxygenated air may be ambient air supplemented daily through mechanisms including impellers for mechanical agitation of the liquid, and air spargers for supplying bubbles of gas to the liquid for dissolution of oxygen into the liquid.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, isopropyl, propanol, butanol, pentanol, hexanol, isobutanol, and/or glycerol; fats and oils such as soybean oil, rice bran oil, canola oil, olive oil, corn oil, sesame oil, and/or linseed oil; etc. These carbon sources may be used independently or in a combination of two or more.

In one embodiment, the method comprises use of two carbon sources, one of which is a saturated oil selected from canola, vegetable, corn, coconut, olive, or any other oil suitable for use in, for example, cooking. In a specific embodiment, the saturated oil is 15% canola oil or discarded oil that has been used for cooking.

In one embodiment, the microorganisms can be grown on a solid or semi-solid substrate, such as, for example, corn, wheat, soybean, chickpeas, beans, oatmeal, pasta, rice, and/or flours or meals of any of these or other similar substances.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, sodium chloride and/or sodium carbonate. These inorganic salts may be used independently or in a combination of two or more.

In some embodiments, the method for cultivation may further comprise adding additional acids and/or antimicrobials in the liquid medium before and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control undesriable bacterial growth.

In one embodiment, the subject invention provides methods of producing a microbial metabolite by cultivating a microbe strain of the subject invention under conditions appropriate for growth and production of the metabolite; and, optionally, purifying the metabolite. In a specific embodiment, the metabolite is a biosurfactant. The metabolite may also be, for example, ethanol, lactic acid, beta-glucan, proteins, amino acids, peptides, metabolic intermediates, polyunsaturated fatty acids, and lipids. The metabolite content produced by the method can be, for example, at least 20%, 30%, 40%, 50%, 60%, 70%, 80%, or 90%.

The biomass content of the fermentation medium may be, for example from 5 g/l to 180 g/l or more. In one embodiment, the solids content of the medium is from 10 g/l to 150 g/l.

In the case of a dried product, or a culture produced using solid state fermentation or modifications thereof, the cell concentration may be, for example, $1 \times 10^9$, $1 \times 10^{10}$, $1 \times 10^{11}$, $1 \times 10^{12}$ or $1 \times 10^{16}$ cells per gram of final dried product.

The microbial growth by-product produced by microorganisms of interest may be retained in the microorganisms or secreted into the growth medium. In another embodiment, the method for producing microbial growth by-product may further comprise steps of concentrating and purifying the microbial growth by-product of interest. In a further embodiment, the medium may contain compounds that stabilize the activity of microbial growth by-product.

In one embodiment, all of the microbial cultivation composition is removed upon the completion of the cultivation (e.g., upon, for example, achieving a desired cell density, or density of a specified metabolite). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a microbe-free medium or contain cells, spores, mycelia, conidia or other microbial propagules. In this manner, a quasi-continuous system is created.

Advantageously, the methods of cultivation do not require complicated equipment or high energy consumption. The microorganisms of interest can be cultivated at small or large scale on site and utilized, even being still-mixed with their media. Similarly, the microbial metabolites can also be produced at large quantities at the site of need.

Because, in certain embodiments, the microbe-based products can be generated locally, without resort to the microorganism stabilization, preservation, storage and transportation processes of conventional microbial production, a much higher density of live microbes, spores, mycelia, conidia or other microbial propagules can be generated, thereby requiring a smaller volume of the microbe-based product for use in the on-site application or which allows much higher density microbial applications where necessary to achieve the desired efficacy. This allows for a scaled-down bioreactor (e.g., smaller fermentation tank, smaller supplies of starter material, nutrients and pH control agents), which makes the system efficient. Local generation of the microbe-based product also facilitates the inclusion of the growth broth in the product. The broth can contain agents produced during the fermentation that are particularly well-suited for local use.

Locally-produced high density, robust cultures of microbes are more effective in the field than those that have undergone vegetative cell stabilization, have been sporulated or have been sitting in the supply chain for some time. Reduced transportation times allow for the production and delivery of fresh batches of microbes and/or their metabolites at the time and volume as required by local demand.

Advantageously, local microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell- and/or propagule-count product and the associated broth and metabolites in which the microbes are originally grown.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

Preparation of Microbe-Based Products

The subject invention provides microbe-based products for use improved recovery of oil from oil sands. One microbe-based product of the subject invention is simply the fermentation medium containing the microorganism and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

In one exemplary embodiment, the microbe-based composition of the subject invention comprises a yeast fermentation product useful for detaching oil from oil sands, the product comprising fermentation broth in which *Starmerella bombicola* yeast cells are cultivated. *S. bombicola* produces a sophorolipid layer when cultivated in a nutrient medium comprising, for example, glucose, urea, yeast extract, vegetable oil and optionally, antimicrobial substances to prevent contaminating bacterial growth. After, for example, about 5 days of culture at 25° C. and pH 3.5, the final concentration of SLP is about, for example, 10-15% of the working volume. Once the SLP settles, it can be harvested. The remaining supernatant can be applied directly to oil sands. This supernatant can comprise, for example, 1-5 g/L of residual SLP, as well as leftover cell biomass and other growth by-products.

If desired, the harvested SLP can also be applied directly to oil sands according to the subject invention, without processing, or the SLP can be purified, diluted, or processed in any way prior to being applied to the oil sands. When use of another biosurfactant is desired, a similar product is envisioned that utilizes any other microbe capable of producing the other biosurfactant.

In one exemplary embodiment, the composition comprises a yeast fermentation product that can be obtained via cultivation of *Wickerhamomyces anomalus*(*Pichia anomala*), *Pichia occidentalis*, *Pichia guilliermondii* or another *Pichia* yeast. This yeast fermentation product can be useful for, for example, reducing viscosity and/or increasing API gravity of heavy oils. In one embodiment, the nutrient medium comprises sources of carbon, nitrogen, minerals and optionally, one or both of an antimicrobial substance to prevent contaminating bacterial growth and an additional carbon source. Typically, with submerged fermentation, the pH begins at 5.0-5.5, then decreases to 3.0-3.5, where it is stabilized. The fermentation medium, harvested after, for example, 24 to 96 hours of cultivation at 25-30° C., can comprise yeast cell biomass, residual nutrients, and microbial growth by-products (e.g., biosurfactants, oxidizing enzymes, hydrolyzing enzymes, and/or solvents). Alternatively, the culture can be grown using a modified form of SSF, where a solid substrate with ample surface area onto which the yeasts can attach and propagate is used, e.g., rice, soybeans, chickpeas, pasta, oatmeal or beans. The entire substrate with yeast cells growing throughout, can be blended, milled and/or micronized, and optionally, dried to form the yeast fermentation product.

The microorganisms in the microbe-based product may be in an active or inactive form. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

The microbes and/or medium (e.g., broth or solid substrate) resulting from the microbial growth can be removed from the growth vessel and transferred via, for example, piping for immediate use.

In one embodiment, the microbe-based product is simply the growth by-products of the microorganism. For example, biosurfactants produced by a microorganism can be collected from a submerged fermentation vessel in crude form, comprising, for example, about from 0.001% to 99% pure biosurfactant in liquid broth In other embodiments, the microbe-based product (microbes, medium, or microbes and medium) can be placed in containers of appropriate size, taking into consideration, for example, the intended use, the contemplated method of application, the size of the fermentation vessel, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

Upon harvesting, for example, the yeast fermentation product, from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, solubility controlling agents, emulsifying agents, biocides, other microbes, lubricants, stabilizers, ultra-violet light resistant agents and other ingredients specific for an intended use.

In one embodiment, the product may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, sodium hydroxide, ammonium hydroxide, potassium carbonate or bicarbonate, hydrochloric acid, nitric acid, sulfuric acid or a mixture.

In one embodiment, additional components such as an aqueous preparation of a salt as polyprotic acid such as sodium bicarbonate or carbonate, sodium sulfate, sodium phosphate, sodium biphosphate, can be included in the formulation.

Advantageously, in accordance with the subject invention, the microbe-based product may comprise medium in which the microbes were grown. The product may be, for example, at least, by weight, 1%, 5%, 10%, 25%, 50%, 75%, or 100% medium (e.g., broth). The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

Methods of Enhanced Oil Recovery

In one embodiment, the subject invention provides a method for recovering oil from oil sands comprising contacting a microbe-based composition of the subject invention with the oil sands or to a site (e.g., formation) containing oil sands. The method can also be used to convert heavy oil and/or bitumen to light oil, e.g., by reducing its viscosity and/or increasing its API gravity. The method optionally includes applying biosurfactants, pH adjusters, and/or other agents along with the microbe-based composition.

In one embodiment the subject invention provides improved methods of recovering oil from oil sands or a formation containing oil sands, wherein the method comprises: applying a microbe-based composition comprising one or more biochemical-producing microorganisms and/or their growth by-products to the oil sands, or to the formation containing oil sands, thereby causing the oil to detach from the oil sands; and recovering the detached oil from the oil sands or from the formation. In certain embodiments, the recovered oil is bitumen or heavy oil.

As used herein, "applying" a composition or product refers to contacting it with a target or site such that the composition or product can have an effect on that target or site. The effect can be due to, for example, microbial growth and/or the action of a biosurfactant or other microbial growth by-product. For example, the method can be performed in situ by applying the composition and/or other agents directly to an oil sands field. Additionally, the composition can be contacted with oil sands that have already been mined from the earth. The method can be useful for oil sands found at any depth below the earth's surface; thus, the method can optionally be used in combination with existing on-site mining and/or in situ drilling operations.

The subject invention can be applied during all stages of the chain of operations, including exploration and production (E&P) operators (e.g., onshore and offshore wellbores, flowlines, and tanks), midstream (e.g., pipelines, tankers, transportation, storage tanks), and in refineries (e.g., heat exchangers, furnaces, distillation towers, cokers, hydrocrackers).

In certain embodiments, the method utilizes a microbe-based composition comprising *Starmerella bombicola* culture to detach the oil from the oil sands. The microbes can be live (or viable) or inactive at the time of application. Advantageously, the microbe-based composition is capable of increasing the wettability of the oil sands, allowing for detachment of the oil and/or bitumen from the clay, sand, and other minerals present in oil sands.

In one embodiment the microbe-based composition comprises the fermentation medium in which the microorganism (e.g., the *Starmerella bombicola*) and/or microbial growth by-product was produced. In one embodiment, the microbe-based composition comprises a microbial growth by-product without the microorganism that produced it. In certain embodiments, the growth by-products are in addition to any biochemicals produced by the microorganisms of the microbe-based composition, meaning the additional materials are produced separately.

In one embodiment, the microbial growth by-product is a biosurfactant. For example, pure or crude form biosurfactants can be applied to not only enhance detachment of oil from oil sands, but also to enhance the recovery of oil by reducing the interfacial tension between the oil and oil sands and/or between oil and formation rock.

The biosurfactants can be selected from glycolipids, e.g., sophorolipids, mannosylerythritol lipids, trehalose lipids and rhamnolipids, and lipopeptides, e.g., surfactin, iturin, lichenysin and fengycin. In one exemplary embodiment, the biosurfactants are sophorolipids (SLPs) and/or mannosylerythritol lipids (MELS) at a concentration of, for example, 0.1% to 10.0% or higher.

In one embodiment, the method can further comprise applying a basic substance to the oil sands or oil sands formation with the microbe-based composition and/or biosurfactants. The basic substance preferably keeps the composition at a pH of about 7.0 to 10.5, more preferably about 10.0 to 10.5. The basic substance can be, for example, potassium hydroxide, sodium hydroxide and/or ammonium hydroxide.

In certain embodiments, the method further comprises subjecting the oil sands to cavitation after applying the microbe-based composition thereto. In one embodiment, the oil sands have been mined from the earth prior to being treated according to the subject invention.

In one embodiment, the method can further comprise treating the oil recovered from the oil sands and/or oil sands formation to reduce the viscosity and/or increase the API gravity of the oil. For example, a microbe-based composition of the subject invention can be applied directly to the recovered oil, followed by, optionally, subjecting the oil to cavitation. Preferably, the microbe-based composition utilized for reducing viscosity and/or increasing API gravity of oil comprises a *Pichia* yeast culture, such as *Pichia anomala* (*Wickerhamomyces anomalus*), *Pichia guilliermondii*, and/or *Pichia occidentalis*.

Optionally, heat exchangers or another heat source can be used throughout the method, for example, between 30° C. to 60° C., preferably between 40° C. to 50° C. However, in one embodiment, temperature does not need to be increased and the process can be carried out at ambient temperatures. Advantageously, this results in reduced energy consumption.

According to this method, the sands and other solid particles present in the mixture will settle out of the mixture, and the oil and other composition liquids can be piped to, for example, a storage tank, where they can further be separated from one another using known methods.

Cavitation can be carried out using machinery known in the art, and can comprise, for example, hydrodynamic or ultrasonic methods.

As used herein, "cavitation" in the context of treating heavy oil means the formation, growth, and collapse or implosion of gas or vapor filled bubbles in liquids. Cavitation requires the presence of small and transient microcavities or microbubbles of vapor or gas, which grow and then implode or collapse. During cavitation of heavy oil, a portion of the liquid comprising the heavy oil is in the form of a gas, which is dispersed as bubbles in the liquid portion. The process effectively destructures the molecular arrangement of heavy hydrocarbons in oil (e.g., asphaltenes, which can form highly associative and cohesive aggregates), thereby reducing its viscosity.

In hydrodynamic cavitation, the liquid comprising the heavy oil is passed through a restriction or cavitation zone, such as, for example, a capillary or nozzle, to increase the velocity of the mixture. The gaseous portion may be present prior to passing the liquid comprising the heavy oil through the cavitation zone and/or such gaseous portion may be produced as a result of the pressure drop that results from passing the liquid comprising the heavy oil through the cavitation zone.

In ultrasonic cavitation, sound waves are propagated into the liquid, resulting in alternating high and low pressure cycles. During the low pressure cycle, high intensity ultrasonic waves create small vacuum bubbles or voids in the liquid. When the bubbles attain a volume at which they can no longer absorb energy, they collapse violently during a high pressure cycle.

Cavitation according to the subject methods can be applied to heavy crude oil at any point during the oil recovery and transport chain of operation in order to prevent or reduce sedimentation of heavy hydrocarbons in the crude fluids, for example, after recovery from oil sands and before being placed in a collection tank; during storage; after storage in a collection tank and before being transported in a tanker; during transportation; before the refining process, etc. Cavitation machinery can be attached to a storage tank, tanker truck, pump system, piping, tubing, and/or any other equipment used for transport, transmission and/or storage of crude oil.

In one embodiment, the present invention allows for improved transportation of oil. By reducing the viscosity and/or increasing the API gravity of heavy oil, oils can be more efficiently transported by pipeline, tanker trucks and/or cargo trains.

Advantageously, the subject invention can increase the API gravity of crudes, heavy crudes, bitumens, tar sands and petcokes, as well as reduce or eliminate the need for, and costs associated with, steam injection and other thermal, chemical and mechanical methods of heavy oil extraction. Further reduced or eliminated are the need for diluents (e.g., light or refined crude oil) and water jackets to help move heavy crude through pipelines. Even further, with the reduction of heavy oil viscosity, transportation of oil is faster and less costly.

Advantageously, the methods can increase the amount of upgraded, usable, and valuable oil products that can be produced from oil sands containing heavy oils and/or bitumen, for example, by decreasing the BTU of the heavy oil prior to refining. In other words, because the oil has been treated prior to refining, more useful products such as fuel oils, kerosene, and diesel fuel, and less petcoke, for example, can be produced using less complex refining processes than if the oil were left untreated and highly viscous. Furthermore, the subject invention can be used without increasing the TAN of oil.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1

Fermentation of *Starmerella bombicola* For Sophorolipid (SLP) Production in a 550 Gallon Reactor A portable, fully enclosed reactor, designed specifically for yeast growth and biosurfactant production, is operated by PLC and comprises water filtration, a temperature control unit, an impeller and a microsparger. The reactor has a working volume of 500 gallons when growing *S. bombicola* for SLP production.

In preferred embodiments, the nutrients for SLP production comprise glucose, urea, yeast extract, and vegetable oil.

The reactor is inoculated with 50 liters of liquid seed culture grown in another reactor. The duration of the cultivation cycle for SLP production is about 5 days, at 25° C. and pH 3.5. The final concentration of SLP is roughly 10-15% of working volume, containing 70-75 gallons of SLP.

The culture can be collected into a separate tank. After SLP is allowed to settle to the bottom of the tank, it can be removed and processed as desired. The remaining (approximately) 420 gallons of culture in the tank can comprise from 3-5 g/L of residual SLP.

Example 2

Fermentation of *Wickerhamomyces anomalus* for Producing Cell Biomass

A movable airlift reactor operated by PLC with water filtration, temperature control unit, and microsparger for sufficient aeration is used. The process can be carried out as batch cultivation process. The 800 gallon reactor is specifically designed for growing yeasts and has a working volume of 700 gallons when growing *Wickerhamomyces*.

The nutrients comprise glucose, urea, yeast extract, and, optionally, vegetable oil. Inoculation of this reactor requires up to 5% liquid seed culture of working volume. The duration of the cultivation cycle is 24-96 hours, at a temperature 25-30° C. and pH 3.5-4. The final product comprises 25-30 gallons of liquid culture.

REFERENCES

PetroWiki. *Heavy Oil*. SPE International; [updated 19 Jan. 2016; accessed 7 Feb. 2017]. http://petrowiki.org/Heavy_oil #cite_note-r1-1. ("Heavy Oil" 2016).

We claim:

1. A method for enhancing oil recovery from oil sands or from a formation containing oil sands, wherein the method comprises applying to the oil sands or the formation a composition comprising one or more microbial growth by-products without a living microorganism that produces the growth by-products, wherein the microorganism is a *Starmerella bombicola* yeast and the growth product is a sophorolipid, and wherein the application of the composition causes oil to detach from the oil sands; subjecting the oil sands to cavitation; and recovering the detached oil from the oil sands or from the formation.

2. The method of claim 1, wherein the detached oil is heavy oil or bitumen.

3. The method of claim 1, wherein the composition is contacted with oil sands that have been mined from the earth.

4. The method of claim 1, wherein applying the composition comprises injecting the composition into a formation containing oil sands.

5. The method of claim 1, wherein the concentration of sophorolipids in the composition is from 0.1% to 10.0%.

* * * * *